United States Patent
Kretschmer et al.

(10) Patent No.: US 10,922,853 B2
(45) Date of Patent: Feb. 16, 2021

(54) REFORMATTING WHILE TAKING THE ANATOMY OF AN OBJECT TO BE EXAMINED INTO CONSIDERATION

(71) Applicant: Siemens Healthcare GmbH, Erlangen (DE)

(72) Inventors: Jan Kretschmer, Nuremberg (DE); Grzegorz Soza, Heroldsberg (DE); Michael Suehling, Erlangen (DE); Christian Tietjen, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/502,334

(22) PCT Filed: Aug. 13, 2015

(86) PCT No.: PCT/EP2015/068636
§ 371 (c)(1),
(2) Date: Feb. 7, 2017

(87) PCT Pub. No.: WO2016/026759
PCT Pub. Date: Feb. 25, 2016

(65) Prior Publication Data
US 2017/0236308 A1 Aug. 17, 2017

(30) Foreign Application Priority Data
Aug. 22, 2014 (DE) .................. 10 2014 216 702

(51) Int. Cl.
*G06T 11/00* (2006.01)
*G06T 19/00* (2011.01)
(Continued)

(52) U.S. Cl.
CPC ............ *G06T 11/003* (2013.01); *A61B 34/10* (2016.02); *G06T 3/0031* (2013.01); *G06T 7/70* (2017.01);
(Continued)

(58) Field of Classification Search
None
See application file for complete search history.

(56) References Cited

U.S. PATENT DOCUMENTS

| 2002/0190980 A1 | 12/2002 | Gerritsen |
| 2006/0235294 A1 | 10/2006 | Florin |

(Continued)

FOREIGN PATENT DOCUMENTS

| CN | 101204088 A | 6/2008 |
| CN | 101650835 A | 2/2010 |

(Continued)

OTHER PUBLICATIONS

Kanitsar et al.: "Advanced Curved Planar Reformation: Flattening of Vascular Structures", Inst. of Computer Graphics and Algorithms, Vienna University of Technology, XP031173479; pp. 43-50; DOI: 10.1109/VISUAL.2003.1250353; ISBN: 978-0-7803-8120-9;VIS 2003. IEEE Visualization 2003; Proceedings. Seattle, WA, Oct. 19-24,; 2003.

(Continued)

Primary Examiner — Vikkram Bali
(74) Attorney, Agent, or Firm — Harness, Dickey & Pierce, P.L.C.

(57) ABSTRACT

The invention relates to a method for imaging a three-dimensional object to be examined. According to said method, a three-dimensional parameterized area is determined which is in conformity with an anatomic structure of the three-dimensional object to be examined. The three-dimensional parameterized area is imaged onto a two- (Continued)

dimensional parameterized area. The three-dimensional object to be examined is represented by imaging pixels that are associated with the three-dimensional parameterized area onto the two-dimensional parameterized area. The invention further relates to a method for determining a camera position in a three-dimensional image recording of an object to be examined. The invention also relates to a method for representing a section of an object to be examined. The invention finally relates to a device for imaging a three-dimensional object to be examined.

20 Claims, 5 Drawing Sheets

(51) Int. Cl.
  *G06T 3/00* (2006.01)
  *A61B 34/10* (2016.01)
  *G06T 7/70* (2017.01)
  *G06T 11/60* (2006.01)
(52) U.S. Cl.
  CPC .............. *G06T 11/60* (2013.01); *G06T 19/00* (2013.01); *A61B 2034/105* (2016.02); *G06T 2207/10081* (2013.01); *G06T 2207/30244* (2013.01); *G06T 2210/41* (2013.01); *G06T 2219/021* (2013.01)

(56) References Cited

U.S. PATENT DOCUMENTS

| | | |
|---|---|---|
| 2008/0049991 A1 | 2/2008 | Gering |
| 2009/0248184 A1 | 10/2009 | Steingart |
| 2009/0303348 A1 | 12/2009 | Inatomi et al. |
| 2011/0142306 A1 | 6/2011 | Nair |
| 2012/0120074 A1 | 5/2012 | Huysmans |
| 2012/0141008 A1 | 6/2012 | Ringl |
| 2013/0077841 A1 | 3/2013 | Wu |
| 2014/0160114 A1 | 6/2014 | Stevenson |

FOREIGN PATENT DOCUMENTS

| | | |
|---|---|---|
| CN | 102118561 A | 7/2011 |
| CN | 103279989 A | 9/2013 |
| EP | 1393259 A1 | 3/2004 |
| WO | WO 2093495 | 11/2002 |
| WO | WO 2011017730 A2 | 2/2011 |

OTHER PUBLICATIONS

Ringl H. et al; "The Skull Unfolded: A Cranial CT Visualization Algorithm for Fast and Easy Detection of Skull Fractures"; Radiology; vol. 255; No. 2; pp. 553-562; ISSN: 0033-8419; DOI:10.1148/radiol.10091096; XP055013821;; 2010.
Ligang Liu: et.al.: "A Local/Global Approach to Mesh Parameterization", in: Eurographics Symposium on Geometry Processing, vol. 27, Nr.5, pp. 1-10, 2008; 2008.
Exploring curved anatomic structures with surface sections, by Saroul et al. IEEE Visualization 2003; Oct. 19-24, 2003.
Saroul et.al., "Distance Preserving Flattening of Surface Sections", IEEE Transactions on Visualization and Computer Graphics, vol. 12, No. 1, Jan.-Feb, 2006, pp. 26-35.
Zollhöfer Michael, et.al. : "GPU based ARAP Deformation using Volumetric Lattices", in: EUROGRAPHICS, 2012; 2012.
"Three-dimensional ct maximum intensity projections of the calvaria: a new approach for diagnosis of craniosynostosis and fractures. American journal of neuroradiology", in: American journal of neuroradiology, 2000, vol. 21(10). pp. 1951-1954.
"Visualization modes for ct colonography using cylindrical and planar map projections", in: Journal of computer assisted tomography, 2000, vol. 24(2), pp. 179-188.
Nonlinear Virtual Colon Unfolding A. Bartroli et al. pp. 411-420 (2001); 2001.
Sorkine Olga, et.al. : "As-Rigid-As-Possible Surface Modeling", in: To appear at the Eurographics Symposium on Geometry Processing, vol. 4, pp. 1-8, 2007; 2007.
Kim S.-J. et al; "Offset Triangular Mesh Using the Multiple Normal Vectors of a Vertex"; Computer-Aided Desgin and Applications, CAD´04; vol. 1; URL: http://ma.gnu.ac.kr/paper/Su-Jin_Kim_Offset_triangular_mesh_using_the_multiple_normal_vectors_of_a_vertex.pdf.; pp. 285-291; 2004.
Auzinger Thomas et al.: "Vessel Visualization using Curved Surface Reformation"; IEEE Transactions on Visualization and Computer Graphics, IEEE Service Center; Los Alamitos, CA, US; Bd. 19; Nr. 12; pp. 2858-2867; XP011529779; ISSN: 1077-2626, DOI:10.1109/TVCG.2013.215; 2013.
"Conformal Virtual Colon Flattening"; Hong Wei, et al.; ACM, 2 Penn Plaza, Suite 701, New York, USA, vol. 2006; XP040038805; ACM SIGGRAPH SPM 2006-ACM Symposium on Solid and Physical Modeling: Wales; ISBN: 1595933581; 2005.
German Office Action dated Nov. 25, 2014.
International Search Report and Written Opinion dated Mar. 22, 2016.
Pinkall, U. et. al., "Computing Discrete Minimal Surfaces and Their Conjugates", Experimental mathematics, 2(1):15-36, 1993.
Kretschmer, J. et. al., "ADR—Anatomy-Driven Reformation", IEEE Trans Vis Comput Graph.; 20(12):2496-505. doi: 10.1109/TVCG.2014.2346405, 2014.
Kabsch, W., "A solution for the best rotation to relate two sets of vectors"; Acta Crystallographica Section A, 32(5):922-923, 1976.
Office Action for Chinese Patent Application No. 201580045170.4 dated Dec. 31, 2019 and English translation thereof.

REFORMATTING WHILE TAKING THE ANATOMY OF AN OBJECT TO BE EXAMINED INTO CONSIDERATION

PRIORITY STATEMENT

This application is the national phase under 35 U.S.C. § 371 of PCT International Application No. PCT/EP2015/068636 which has an International filing date of Aug. 13, 2015, which designated the United States of America and which claims priority to German patent application number DE 102014216702.7 filed Aug. 22, 2014, the entire contents of which are hereby incorporated herein by reference.

FIELD

An embodiment of the invention generally relates to a method for imaging a three-dimensional object to be examined. In addition, an embodiment of the invention generally relates to a device for imaging a three-dimensional object to be examined.

BACKGROUND

Computer-aided visualization methods play an important role in clinical application since they provide a very flexible and effective option for examining data obtained from medical imaging methods. The significance and positive effect of computer-aided workflows on the overall effectiveness of current radiological practice are obvious. However, it is probable that in future it will no longer be possible for trained experts to cope with the evaluation of the ever-increasing quantity of image information without additional help. It is therefore crucial for the processing of medical image information to be configured more effectively. This means that applications need to be sped up without the quality of the work, in particular the accuracy and completeness of the examination and evaluation of the image information, being lost in the process.

It is not just in the field of oncology and traumatology that reconstructions based on computerized tomography are usually the basis for a diagnosis and subsequent treatment. Until now the standard method in diagnostic radiology has been a slice-by-slice examination of standardized views orientated orthogonally to each other. Unfortunately, direct viewing and evaluation is not ideal for many tasks since the anatomical structures do not generally run conformally with the coordinate system of the computer tomograph or the imaging medical device and conventionally have complex forms. For example, bone metastases frequently occur in ribs and in the pelvis in the case of advanced cancers, in particular in the case of prostate cancer or breast cancer, and their discovery and tracking of the metastases is a laborious and time-consuming task even for very experienced radiologists.

Due to the aforementioned difficulties, methods for visualizing recorded medical image data have been developed which consider the specific anatomical circumstances. However, generating meaningful visualizations of medical data sets that are relevant for diagnosis is a very difficult task. Owing to the high geometric complexity of the human body, problems, such as, for example, reciprocal concealment and disturbance of views, frequently occur. Since the variation in anatomical geometry between the individual patients is relatively slight, numerous visualization algorithms have been developed of which many are based on and limited to a specific form of a particular anatomical structure. With this group of methods generally one approach resides in approximating organs or other anatomical structures by way of geometric primitives such as, spheres, cylinders or planes, and this enables simple projection of the surrounding tissue. The methods are conventionally optimized for specific application and focus on particular types of CT function. Typical applications are projections of regions of the heart or tumors. Although the simplicity and intuition of the approach form their strength, in the case of primitives with a closed form it is often not possible to replicate the geometry of a projected anatomical structure sufficiently accurately, and this leads to distortions and concealment in the representation.

To enable more flexible viewing of medical data sets, multiplanar reformatting (MPR) was developed in order to represent reconstructed CT volumes in any oriented planes.

Another type of reformatting, curved planar reformation (CPR) and its derivatives, enables even more flexible cuts through the data sets which are defined by individual geometric central lines or complex central line graphs. CPRs are conventionally applied in the visualization of vessels since the generated cuts permit careful examination of the clearance of the vessels and include valuable anatomical context. In contrast to MPRs, CPRs can be controlled directly by patient-specific anatomical data, and this ultimately leads to more information being condensed in a single 2D view that can be rotated about the longitudinal axis.

One primary problem of this type of image algorithm is that it is based on a particular type of projection. Furthermore, these algorithms do not generally provide any tools for processing distortions that occur and parameterize only single cuts instead of whole volume ranges.

Particular user interfaces for visualizations of various anatomical structures have also been developed. Methods for two-dimensional representation of the colon are one example of measures to improve the unfortunately very error-prone diagnostic methods of modern cancer screenings. Due to their complex form and dimensions, the intestines can only be visualized with great difficulty. To retain the specific form of important features, such as polyps, in an expressive way, intestinal development methods are generally directed particularly toward aspects of parameterization and concealment of features.

One generally very time-consuming issue is the detection of bone lesions. With complex anatomical structures, such as the thorax, it is not just the detection of anomalies that is paramount. The detected metastases also have to be documented. More precisely, the metastases have to be tracked back to the corresponding vertebra in order to be able to correctly identify them. If the thorax is navigated through slice-by-slice, this will become a laborious task since the cross-sections of rib bones are subject to a shift between the slices. There have been attempts to solve this problem in modern segmentation and visualization methods by generating normalized views.

To provide developments for the examination of the skull, screening methods have been developed for the detection of traumas. With the algorithm developed specifically for the skull an elastic grid is placed over the patient's head in order to cover and parameterize the cranial bone. The grid is then used to calculate projections that allow for improved clarity and facilitated traceability of skull injuries compared to the sectional views.

Different difficulties, which shall be briefly explained below, occur with the briefly outlined reformatting methods. One problem lies in that distortions inevitably occur with a normalized representation or a surface representation of an originally much more pronounced structure. These distortions occur in the field of imaging of variations and in the field of representation of volumes. The procedure in the former case shall be called surface parameterization below and in the latter case shall be called volume parameterization. The problem of distortions and minimization thereof in the representation of objects having different forms frequently occurs in the processing of computer graphics. For example, in the case of texture images, bending of surrounding regions and the deformations of surface-based grids and volume grids occur.

Conformal images have the property of imaging conformally, and this is particularly important if it is desirable for the similarity of the object to be imaged to be retained in the projection. The conformity of the images plays an important role in medical image registrations. However, local or global scalings occur even with conformal images. This leads to an enlarged or reduced representation of individual regions and produces an unnatural-looking parameterization result. There are other approaches in which there is an attempt to combine the aim of conformity and the rigidity with each other, and this is also called an ARAP paradigm (ARAP=as rigid as possible). Excessive distortions in length with optimum retention of the conformality in particular at local level are avoided in this connection. In particular, some regions are prevented from being imaged too large or too small and therefore the clarity and user-friendliness of the representation is ensured.

ARAP has previously been used to deform triangular grids (see Sorkine et al. "As rigid as possible surface modeling", Symposium on Geometry processing, volume 4, 2007), in order to parameterize surfaces (see Liu et al. "A local/global approach to grid parameterization", Computer Graphics Forum, volume 27, pages 14951504, Wiley Online Library, 2008) and to deform volumes (see Zollhöfer et al. "GPU based ARAP deformation using volumetric lattices", Eurographics 2012 Short Papers, pages 8588, The Eurographics Association, 2012).

However, with conventional approaches of two-dimensional representation of objects or regions to be examined, there are still limitations in respect of the general applicability of the methods since they are conventionally limited to the representation of particular organs or particular anatomical units, such as, for example, cranial bones. It is often necessary, however, to image broader regions first, and these should then be examined for anomalies. Therefore, one drawback of the conventional approaches is that they can only be applied to particular anatomical structures and, furthermore, cannot be easily expanded to regions surrounding these structures, and this leads to low flexibility of the conventional methods and to a limited field of application of these methods. Furthermore, there is also the problem of distorted two-dimensional images. While there are methods which, as briefly described, can minimize distortions, the distortions basically cannot be eliminated since a compromise always has to be made between conformality and rigidity.

SUMMARY

One embodiment of the present application can be seen in developing a widely applicable method with which an optimally realistic overview representation of a three-dimensional region to be examined is possible. It should be possible to represent the surroundings, i.e. the object in its full breadth and thickness, and not just one slice in the sought overview representation.

At least one embodiment of the present application is directed to method and/or a device.

In at least one embodiment of the inventive method, a three-dimensional parameterized surface is first defined which is conformal with the anatomical structure of the three-dimensional object to be examined. The three-dimensional parameterized surface is then imaged onto a two-dimensional parameterized surface. Finally, the three-dimensional object to be examined is represented two-dimensionally by imaging the image points associated with the three-dimensional parameterized surface onto the two-dimensional parameterized surface. Conformal should in this connection be taken to mean that a three-dimensional surface is adapted to the form of a three-dimensional object. This can be achieved, for example, by an approximation method, for example, by a method which is based on the methods of the smallest spares or similar regression methods or other optimization approaches, or also by an intuitive adjustment by a user. Conformal should in this connection therefore be taken to mean that the parameterized surface describes the center of object or that it describes the surface of the object or that it describes a different surface of importance through the object or an organ or the structure.

In at least one embodiment of the inventive method, a method for determining a camera position in a three-dimensional image recording of an object to be examined includes determining the camera position as orthogonal to a field of up vectors, determined with a vertex skinning technique and applied to a three-dimensional parameterized surface that defines the object to be examined.

In at least one embodiment of the inventive method, a method for representing a section of an object to be examined includes carrying out an embodiment of a method expressed above;

defining a section for representation of the object to be examined by identification in the two-dimensional representation; and carrying out a suitable visualization method in the section for representation.

An inventive device of at least one embodiment for imaging a three-dimensional object to be examined comprises a parameter surface-determining unit. The parameter surface-determining unit is adapted to define a three-dimensional parameterized surface which is conformal with the anatomical structure of the three-dimensional object to be examined. Furthermore, the inventive device comprises a reformatting unit which is adapted to image the three-dimensional parameterized surface onto a two-dimensional parameterized surface. Furthermore, the inventive device has a sampling unit which is adapted to image the three-dimensional object to be examined by imaging image points associated with the three-dimensional parameterized surface onto the two-dimensional parameterized surface. A three-dimensional object can be taken to me an entire organ or body part as well as sections thereof or any partial volume of a three-dimensional object.

At least one embodiment the invention is directed to a computer program product which can be loaded directly into a processor of a programmable evaluation device of a medical imaging system, having program code segments to carry out all steps of at least one embodiment of the inventive method when the program is run in the evaluation device.

Further, particularly advantageous embodiments and developments of the invention result from the claims and the following description, wherein the claims of one category of embodiments can also be developed analogously to the claims of a different category of embodiments.

The invention will be described again below with reference to the accompanying Figures using example embodiments. Identical components are provided with identical or corresponding reference numerals in the various Figures. As a rule, the Figures are not to scale. In the drawings:

DETAILED DESCRIPTION OF THE EXAMPLE EMBODIMENTS

Figure 1:
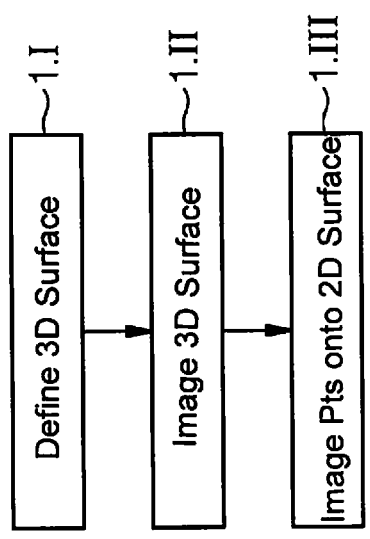
FIG. 1 shows a flow diagram which illustrates a method according to one example embodiment of the invention.

In at least one embodiment of the inventive method, a three-dimensional parameterized surface is first defined which is conformal with the anatomical structure of the three-dimensional object to be examined. The three-dimensional parameterized surface is then imaged onto a two-dimensional parameterized surface. Finally, the three-dimensional object to be examined is represented two-dimensionally by imaging the image points associated with the three-dimensional parameterized surface onto the two-dimensional parameterized surface. Conformal should in this connection be taken to mean that a three-dimensional surface is adapted to the form of a three-dimensional object. This can be achieved, for example, by an approximation method, for example, by a method which is based on the methods of the smallest spares or similar regression methods or other optimization approaches, or also by an intuitive adjustment by a user. Conformal should in this connection therefore be taken to mean that the parameterized surface describes the center of object or that it describes the surface of the object or that it describes a different surface of importance through the object or an organ or the structure.

ARAP optimization methods can be used when determining and optimizing the two-dimensional parameterized surface. In contrast to conventional methods, a surface adjusted exactly to the anatomy is used as the initial surface, however.

One idea in at least one embodiment of the invention can be seen in that the reformatting of the regions to be examined is determined within a wide range by the anatomy of objects to be examined that are also very different. For example, complex and extended structures, such as, for example, skeletal bones, can be detected and represented with the inventive method in such a way that they can be examined quickly. The three-dimensional parameterized surface can be parameterized both continuously and discretely.

An inventive device of at least one embodiment for imaging a three-dimensional object to be examined comprises a parameter surface-determining unit. The parameter surface-determining unit is adapted to define a three-dimensional parameterized surface which is conformal with the anatomical structure of the three-dimensional object to be examined. Furthermore, the inventive device comprises a reformatting unit which is adapted to image the three-dimensional parameterized surface onto a two-dimensional parameterized surface. Furthermore, the inventive device has a sampling unit which is adapted to image the three-dimensional object to be examined by imaging image points associated with the three-dimensional parameterized surface onto the two-dimensional parameterized surface. A three-dimensional object can be taken to me an entire organ or body part as well as sections thereof or any partial volume of a three-dimensional object.

In the method of at least one embodiment, for determining a camera position in a three-dimensional image recording of an object to be examined, the camera position is defined orthogonally to a field of up vectors. The up vectors are determined using a vertex skinning technique, applied to a three-dimensional parameterized surface that defines the object to be examined. The three-dimensional parameterized surface can be the three-dimensional parameterized surface already defined. It can, however, also be an envelope of this surface which has a "more gentle" geometry with fewer sharp curves than the three-dimensional parameterized surface. The up vectors exhibit a field of view or an image in the upward direction.

In the method of at least one embodiment, for representation of a section of an object to be examined, at least one embodiment of the inventive method for two-dimensional imaging of a three-dimensional object to be examined is first carried out. A section for representation of the object to be examined is then defined by identification in the two-dimensional representation. A suitable visualization method is then carried out in the section to be represented. For example, the situation can occur where a section is not optimally represented in the overview representation of the object to be examined. This section can then be prepared for more thorough evaluation by a specific visualization method. For this purpose, for example, the characteristic of a line through a region can be marked in the overview image, wherein the region identified by the line should be detected fully by the additional visualization method. The line can be, for example, what is known as a spline.

At least one embodiment the invention is directed to a computer program product which can be loaded directly into a processor of a programmable evaluation device of a medical imaging system, having program code segments to carry out all steps of at least one embodiment of the inventive method when the program is run in the evaluation device.

An implementation in terms of software of this kind has the advantage that previous evaluation devices of medical imaging devices can be suitably modified by implementing the program in order to inventively carry out an evaluation of generated image data, and this is connected, for example, with the advantages.

Further, particularly advantageous embodiments and developments of the invention result from the claims and the following description, wherein the claims of one category of embodiments can also be developed analogously to the claims of a different category of embodiments.

In an example embodiment of the method for imaging a three-dimensional object to be examined, the three-dimensional parameterized surface is parameterized by a three-dimensional surface grid having a large number of individual elements. In this embodiment, a discrete parameterization of the three-dimensional parameterized surface is chosen therefore. This discrete parameterization can be implemented with relatively low data processing effort and with a high degree of flexibility. The two-dimensional parameterized surface is parameterized with the chosen surface grid by a two-dimensional grid having a large number of individual elements. The two-dimensional representation of the three-dimensional object to be examined occurs by way of imaging of image points associated with the individual elements of the three-dimensional onto the individual elements of the two-dimensional grid. This process is also called resampling.

For example, the last step can be achieved in such a way that the associated image points of the three-dimensional surface grid are associated in the three-dimensional representation with the individual pixels of the two-dimensional grid. For this the pixels of the two-dimensional grid are firstly parameterized by the individual elements, in which they are located, this parameterization is transferred to the individual elements of the three-dimensional surface grid and the associated image point determined in the three-dimensional representation.

As already mentioned, there is a step for acquiring an object to be imaged or the corresponding geometry in the parameterization, for example by segmentation, of this object. For example, model-based parameterized image segmentations can be used here which are based on statistical databases. For adjusting the segmentation to the specific object, statistical means are used first for the individual parameters for initialization. The parameters are then optimized until an optimum adjustment of a grid comprising segments and the dimensions of the object is achieved. An adjustment of a model-based grid can also be enabled, for example, by medical image registration, wherein deformation fields are determined which enable the adjustment of a reference data set to a target data set corresponding to a parameterized object. By using the deformation field, for example particular structures in the reference data set, such as, for example, a central surface between two surfaces, can be imaged from the reference data set onto the patient-specific data set.

The three-dimensional parameterized surface can be an open surface. It can, however, also be a closed surface which is converted before imaging of the three-dimensional parameterized surface onto a two-dimensional parameterized surface into an open three-dimensional parameterized surface. It is crucial that the three-dimensional parameterized surface has an edge during reformatting which can be imaged onto the edge of an initial two-dimensional grid.

When imaging image points associated with the individual elements of the three-dimensional surface grid onto the individual elements of the two-dimensional grid, each pixel in the two-dimensional grid can be parameterized as a function of its position in an individual element of the two-dimensional grid. This parameterization can then be transferred to the three-dimensional surface grid and a 3D position in the three-dimensional surface grid can be calculated for each pixel of the two-dimensional grid, and this matches the position of the pixel in the two-dimensional grid. Finally, an image value associated with the 3D position can be transferred to the associated pixel for each pixel of the two-dimensional grid.

The individual elements can comprise, for example, triangles and/or rectangles and/or hexagons and/or other polygons. The three-dimensional surface grid can be a regular grid or an irregular grid. A regular grid comprises nodes that always have the same valency, whereas this does not need to be the case with an irregular grid.

To obtain optimally distortion-free or low-distortion and rigid as well as conformal two-dimensional imaging, the step of imaging the three-dimensional parameterized surface onto the two-dimensional parameterized surface is achieved by optimizing an energy term associated with the three-dimensional parameterized surface and an energy term associated with a two-dimensional parameterized surface to be optimized.

If the volume around a three-dimensional structure to be represented should also be considered in the two-dimensional imaging of a three-dimensional object to be examined, then a plurality of three-dimensional parameterized offset surfaces, which are conformal with the anatomical structure of the three-dimensional object to be examined, is generated in addition to the three-dimensional parameterized surface. Clearly stated, a type of stack of surface grids or the slices pertaining thereto is produced. Consideration of the volume around a three-dimensional surface structure enables not just the representation of a slice of the object to be examined, but ideally also the representation of the object in its entire breadth and thickness. Therefore, it is not just one surface that is imaged but entire surroundings, i.e. a volume.

A parameterization of the surroundings is therefore obtained which is then deformed (based on the grid including offset surfaces) volumetrically into an unfolded form.

Volumes or a plurality of slices or slice stacks is/are therefore unfolded.

One possibility of generating these parameterized offset surfaces lies in defining the three-dimensional parameterized offset surfaces by determining normal vectors orthogonal to the three-dimensional parameterized surface. The normal vectors are standardized to a particular distance which defines the distance between the offset surfaces and the three-dimensional parameterized center surface.

The offset surface grids of the three-dimensional parameterized offset surfaces can be smoothed by applying grid smoothing methods, for example, Laplacian grid smoothing methods, wherein overlappings of adjacent normal vectors is avoided.

In a simplified embodiment of the inventive method only the middle parameterized surface is optimized in the iterative optimization method of the two-dimensional grid and the structures of the offset surfaces are adjusted accordingly.

Alternatively, the three-dimensional offset surface grids can be explicitly calculated. When imaging these three-dimensional surface grids onto two-dimensional surface grids an energy term associated with the individual surface grids is calculated with an additional shear term and iteratively optimized. Defining a coefficient of the shear term can influence how the ratio of the rigidity to the conformality of the imaging is expressed.

When optimizing the stack of surface grids with the energy term, the rigidity within the slices and the angular distortion between the slices are advantageously modeled separately. In other words, the iteration methods used in respect of the rigidity and conformality can be carried out separately. The energy term specifically allows the shearing or distortion of the slices to be purposefully balanced.

When imaging the three-dimensional parameterized surfaces onto a two-dimensional parameterized surface the local distortion of the imaging can be chosen particularly advantageously as a function of the importance of the image regions of the three-dimensional object. This variant can take into consideration the varying importance of the image regions due to weighting factors in the energy term to be optimized. The particularly important or interesting image regions can therefore be largely kept free of distortions therefore, and the distortions can be "shifted" into less important image regions.

For example, an annotation of points and/or regions and/or structures can be performed as one application. For example, markers can be placed or lesions annotated in the image. Furthermore, an interactive refinement or shifting of the image or reformatting based on the current solution can also be carried out. In the case of shifting, the conformal parameterized three-dimensional surface can be shifted in the normal direction or negative normal direction and be sampled again. Finally, detailed views can also be generated. Because the visuaization is conformal with the structure to be imaged, sections can easily be identified and unfolded again.

In the method for representation of a section of an object to be examined, defining the section to be represented can comprise marking a spline curve in the section to be represented as the center for an image representation with a CPR method as the visualization method. Alternatively, or additionally, an MPR method can also be used as the visualization method.

FIG. 1 illustrates in a flow diagram the individual steps of the method 100 for imaging a three-dimensional object 1 to be examined. In step 1.I a three-dimensional parameterized surface 2 is defined which is conformal with the anatomical structure of the three-dimensional object 1 to be examined. In step 1.II the three-dimensional parameterized surface 2 is imaged onto a two-dimensional parameterized surface 4. Finally, in step 1.III the three-dimensional object 1 to be examined is represented two-dimensionally by imaging image points 5 associated with the three-dimensional parameterized surface 2 onto the two-dimensional parameterized surface 4.

Figure 2:
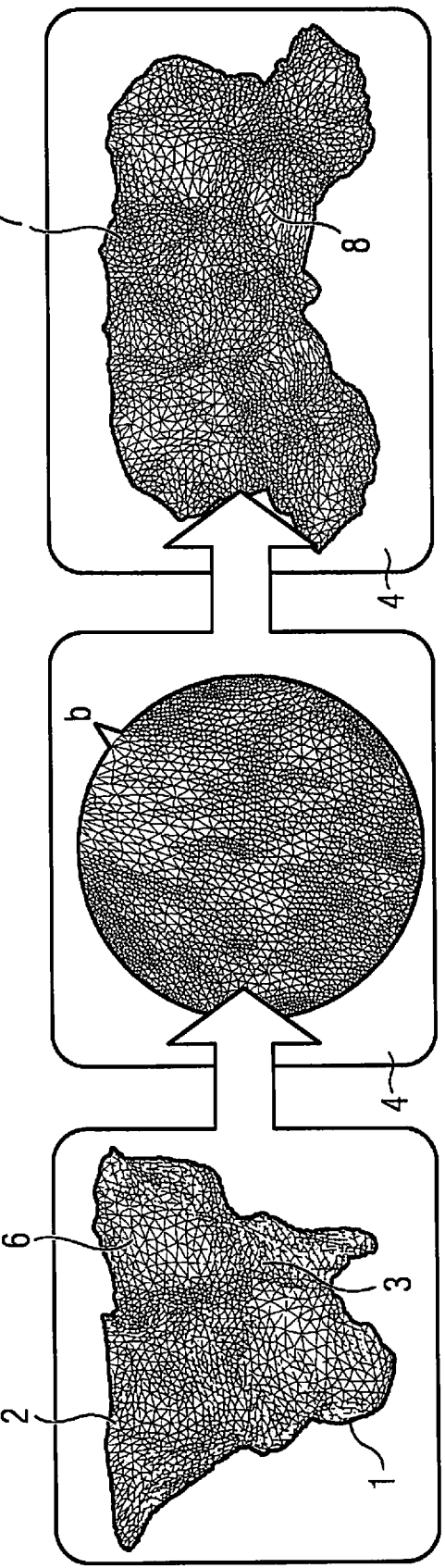
FIG. 2 shows a schematic representation of reformatting according to one example embodiment of the invention.

FIG. 2 illustrates the method steps which the anatomy-controlled reformatting of an object to be examined, in this case a pelvic bone, comprise according to a first example embodiment of the invention. The left-hand partial image shows how an open surface grid 3, centered between the surfaces of the pelvis 1, comprising triangles 6 is defined, with some boundary nodes or boundaries of the surface grid being marked. The three-dimensional surface grid 3 is defined by a list of coordinates $v_i \epsilon R^3$, where $i=0 \ldots n1$, a list of triangles T and a list of half-edges HE. As already mentioned, the surface grid is an open grid with a boundary.

The middle partial image of FIG. 2 shows how the three-dimensional surface grid is imaged onto an initial two-dimensional surface 4. Chosen as the initial two-dimensional surface is a circular surface, onto whose circumference b the boundary nodes or boundaries of the surface grid are imaged. The boundary nodes serve as boundary conditions for the calculation of the remaining nodes $v_i'$ of the two-dimensional grid. The use of a circular surface as an initial surface is chosen purely for the sake of simplicity and other initial surfaces may also be chosen as an alternative. The following discrete linear Poisson equation system is calculated for determining the remaining nodes $v_i'$ on the initial two-dimensional surface:

$$\#V(i)v_i' - \sum_{j\in V(i)\cap \Omega} v_j' = \sum_{j\in V(i)\cap \Omega} v_j' \quad (1)$$

Here $v_i'$ represents all free nodes which are not located on the circumference $\Omega$ (also designated b in FIG. 2). V(i) designates the set of adjacent nodes of a node $v_i'$ and #V(i) the size of the set of adjacent nodes, i.e. the number of valencies. The nodes $v_j'$ indicated by j are the nodes adjacent to node $v_i'$. These can be nodes already defined on the edge, i.e. the circumference, which are on the right-hand side of the equation 1, or be free adjacent nodes which are not located on the circumference and are associated with the total to the left of the equals sign in equation 1.

An optimization process is then carried out starting from this initial surface or this initial grid, with a 2D rotation being calculated first of all in a local optimization step for each triangle, and this defines the rotation $R_t$ of the triangle between the 3D representation and the ideal, undistorted arrangement of the triangle subsequently subject to a global iterative optimization process.

For imaging the triangles from the 3D representation onto the initial surface, first of all imaging $N_t:R^3>R^2$ that retains the form of the triangle is defined.

$$N_t(x) = \left( \frac{v_b - v_a}{\|v_b - v_a\|} \frac{n\times(v_b - v_a)}{n\times\|v_b - v_a\|} \right)^T \left( x - \frac{1}{3}(v_a + v_b + v_c) \right) \quad (2)$$

where $n = \frac{(v_c - v_a)\times(v_b - v_a)}{\|(v_c - v_a)\times(v_b - v_a)\|}$ Here a, b and c are the indices of the nodes of a triangle $t_t$.

For calculating the rotation between the triangle $t^0_t$ projected onto the 2D dimension, where $$t^0_t = (v_a^0, v_b^0, v_c^0)_t = (N_t(v_a), N_t(v_b), N_t(v_c)) \quad (3)$$

and for the triangle of the current solution to the optimization method $(v_a', v_b', v_c')$, for example, the Kabsch algorithm can be used which is described in W. Kabsch "A solution for the best rotation to relate two sets of vectors"; Acta Crystallographica Section A, 32(5):922-923, 1976. First of all, a single value breakdown $A = VSW^T$ of the covariant matrix A of the nodes is calculated relative to the focus of the current triangles.

$$A = v_a^0(v_a'-c)^T + v_b^0(v_b'-c)^T + v_c^0(v_c'-c)^T \quad (4)$$

Here $c=\frac{1}{3}(v_a'+v_b'+v_c')$ indicates the focus of the current triangles underlying the optimization method.

The rotation $R_t$ between the original undistorted triangles, but which have already been projected onto the 2D surface, and the current triangles underlying the optimization method then results as $$R_t = W \begin{pmatrix} 1 & 0 \\ 0 & \text{sign}(\det(WV^T)) \end{pmatrix} V^T \quad (5)$$

In a global optimization step, hereinafter also called a global phase, the individually rotated triangles have to be joined together again in the two-dimensional representation for the detected optimum rotations $R_t$, so a connected surface results. The sought positions of the nodes v'$_i$ result from the following optimized energy functional:

$$E_{ARAP}(v'_i, R) = \frac{1}{2} \sum_{(i,j)\in HE} \cot(\Theta_{i,j}) \|(v'_i - v'_j) - R_{t(i,j)}(v^0_i - v^0_j)\|^2 \quad (6)$$

Here $\cot(\theta_{i,j})$ are cotangential weights, as are described in U. Pinkall and K. Polthier "Computing discrete minimal surfaces and their conjugates" Experimental mathematics, 2(1):15-36, 1993. HE are sets of half-edges in the grid, $R_{t(i,j)}$ is the rotation of a triangle with the half-edge (i, j), $v_i^0 \in \Re^3$ are the node positions of the original triangles and $v'_i \in \Re^2$ are the nodes to be optimized. To facilitate calculation of the target nodes, the rotations $R_{t(i,j)}$ determined in the local optimization process are maintained, so a linear equation system results with optimization. In other words, the rotations $R_t$ and the nodes v'$_i$ are optimized in separate steps. Once the equation system (6) has been solved, i.e. the nodes v'$_i$ have been determined or optimized, the corresponding rotations $R_{t(i,j)}$ are then re-calculated and the optimization step of the nodes then repeated, so an iterative optimization method results.

During optimization, the gradient of the energy $E_{ARAP}$ is set at 0. The following linear equation system results therefore:

$$\sum_{j\in V(i)} (\cot(\Theta_{i,j}) + \cot(\Theta_{j,i}))(v'_i - v'_j) = \\ \sum_{j\in V(i)} (\cot(\Theta_{i,j})R_{t(i,j)} + \cot(\Theta_{j,i})R_{t(j,i)})(v^0_i - v^0_j) \quad (7)$$

where i=i . . . N1.

To summarize, the optimization method is identified by a local phase with calculation of rotations between the original or optimized triangles and the triangles of the respective current iterative solution and by a global phase in which an energy term, which is associated with the grid having optimally rotated triangles, is minimized. The two steps comprising the local phase and the global phase are alternately repeatedly carried out in an iterative method. The approach with a local and a global phase has the advantage that the rotations are fixed in the global phase, i.e. are not unknowns. This means that the optimization problem becomes linear and can be described with the aid of a matrices, i.e. in a linear equation system. The optimization does not necessarily have to take place in this manner, however. The energy functional of equation 6 could also be minimized directly.

The right-hand partial image of FIG. 2 shows the result of this iterative process. It is a two-dimensional grid 7 whose grid element 8 have an optimum similarity to the grid elements 6 of the three-dimensional surface grid 3.

Figure 3:
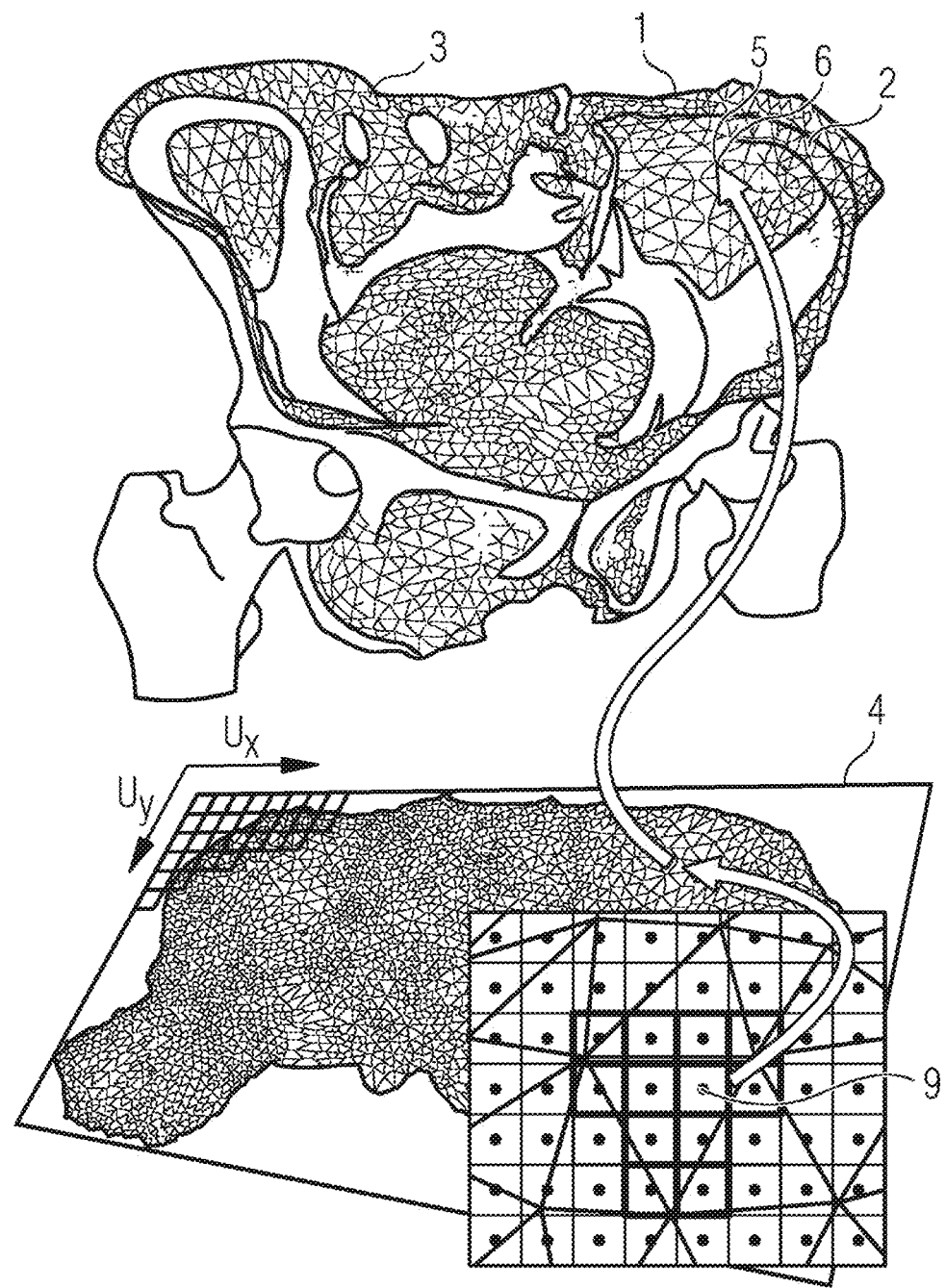
FIG. 3 shows a schematic view of a sampling step for generating a two-dimensional representation.

In the first example embodiment of the inventive method a sampling step follows next, with an image value or an intensity value of the corresponding position in the three-dimensional surface grid being associated with each of the pixels in the two-dimensional grid. This procedure is illustrated in FIG. 3. This method step is also called resampling. With resampling, once each of the optimum node positions v'$_i$ have been calculated, point-by-point sampling of the three-dimensional surface grid and imaging onto the pixels of the two-dimensional imaging are implemented in conjunction with the original three-dimensional surface grid. To attain an image, hereinafter also called an ADR image, having the properties of the three-dimensional image, with a particular resolution $ADR_{resx}*ADR_{resy}$ from the two-dimensional grid, first of all the extent of the ADR image is defined with boundary values v'$_{min}$ and v'$_{max}$ in the x and y directions. Coordinates $u_i$ of the ADR image can be determined on this basis:

$$u_i = \begin{pmatrix} u_{ix} \\ u_{iy} \end{pmatrix} = \begin{pmatrix} (v'_{ix} - v'_{minx})\frac{ADR_{resx}}{v'_{maxx} - v'_{minx}} \\ (v'_{iy} - v'_{miny})\frac{ADR_{resy}}{v'_{maxy} - v'_{miny}} \end{pmatrix} \quad (8)$$

To determine the intensity of the pixels of the ADR image, first of all the corresponding triangle is determined in the ADR image, in which the corresponding pixel is positioned. The barycentric coordinates of the pixel are calculated and the corresponding position in the 3D surface grid calculated. Scanning of the volume at the corresponding position in the 3D representation then produces the intensity value for the associated pixel. A lookup table can also be calculated to accelerate the search for the triangle with which the pixel is associated. In the lookup table, all triangles which overlap the pixel are associated with each pixel (with fine triangle grids, the triangles can be smaller locally than the pixel in the target image and vice versa. Barycentric coordinates then only have to be calculated for these triangles (and not for all triangles).

In the first example embodiment illustrated in FIGS. 2 and 3 only one reformatted 2D image of a single cut surface is generated. However, in the examination of volumetric medical data sets it is often necessary to inspect the surroundings of a particular region more closely by looking at adjacent slices of the reconstructed image. The method outlined in FIGS. 2 and 3 can also be applied to speed up this type of medical examination and make it more flexible. In this case the method is not limited to the visualization of a single surface of the 3D representation and instead the surroundings or surrounding volume of a parameterized surface can also be included.

Figure 4:
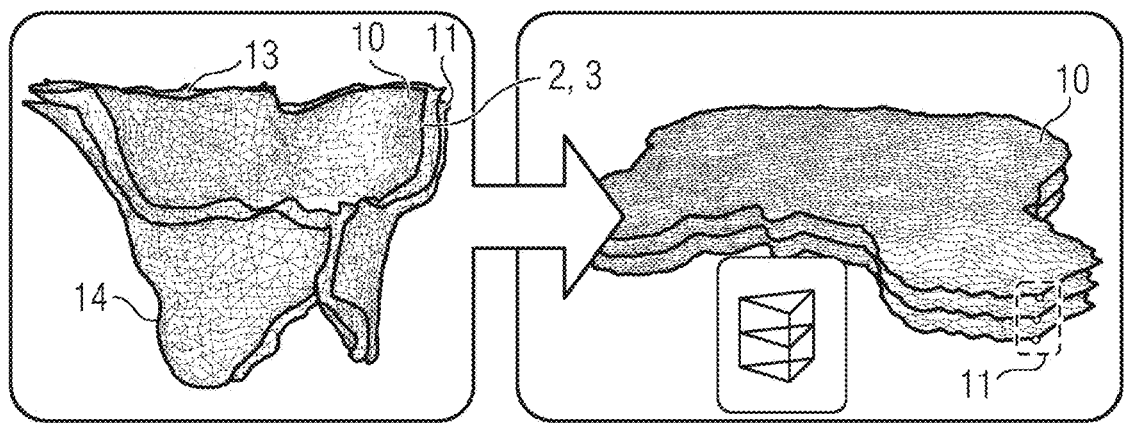
FIG. 4 shows reformatting of a volume within the context of one example embodiment of the inventive method.

In a second example embodiment, the surroundings of a surface parameterized as in FIG. 2 is parameterized by calculating the already parameterized surface of what are known as offset surfaces 10, 11 or offset surface grids 13, 14. In the simplest case an offset surface 10, 11 or an offset surface grid 13, 14 is calculated for this purpose on both sides of the already parameterized surface. This procedure is illustrated in FIG. 4. The offset surface grids 13, 14 shown there are, for example, simple copies of the already parameterized three-dimensional grid 3 of the already parameterized central surface 2 in the positive and negative directions of a normal relative to the parameterized surface. The nodes consequently have the position v=v dn and v+=v+dn, where d is a defined distance of the offset surfaces from the central surface and n is the normal onto the central surface at the position of the nodes v. If reformattings with constant thickness are to be generated, then d is defined as constant over the entire parameterized surface or over the entire ADR surface, so instead of a single two-dimensional ADR surface, a stack of three ADR surfaces is produced in the reformatting, as is shown in the right-hand component drawing in FIG. 4.

Figure 5:
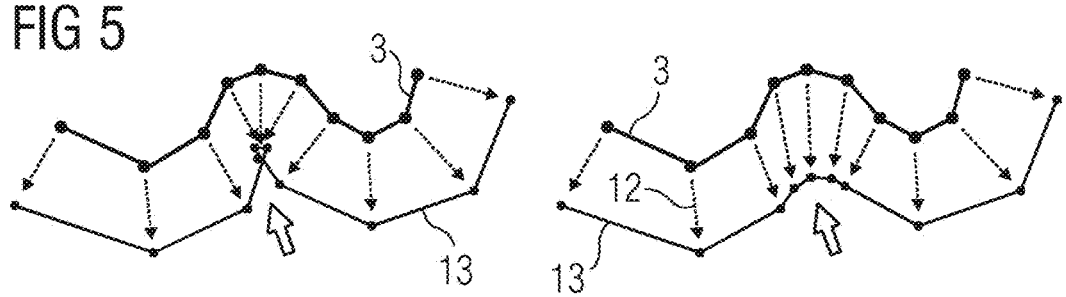
FIG. 5 shows the overlappings of surface elements that occur during formation of offset surfaces.

In the simplest variant of the second embodiment only the middle three-dimensional parameterized surface is projected onto a 2D surface therefore and the two offset surface grids 13, 14 have the same geometry as the central surface. This procedure is shown in the left-hand component drawing of FIG. 5. The sampling step is particularly simple in this case because the grid structure is identical in each case in the various offset grids 13, 14. However, what are known as self-overlappings frequently occur with this approach when the shifted offset grids 13, 14 for the parameterization of the shifted offset surfaces are calculated. More precisely, the normals 12, with which the offset grids are to be defined, overlap. This phenomenon is also shown in the left-hand component drawing in FIG. 5. To reduce the self-overlappings, the positions of the nodes of the offset grids are corrected in such a way that they are no longer located on the normals 12 of the nodes of the three-dimensional ADR surface, and this is shown in the right-hand component drawing in FIG. 5. However, distortions are connected therewith in the two-dimensional representation.

Figure 6:
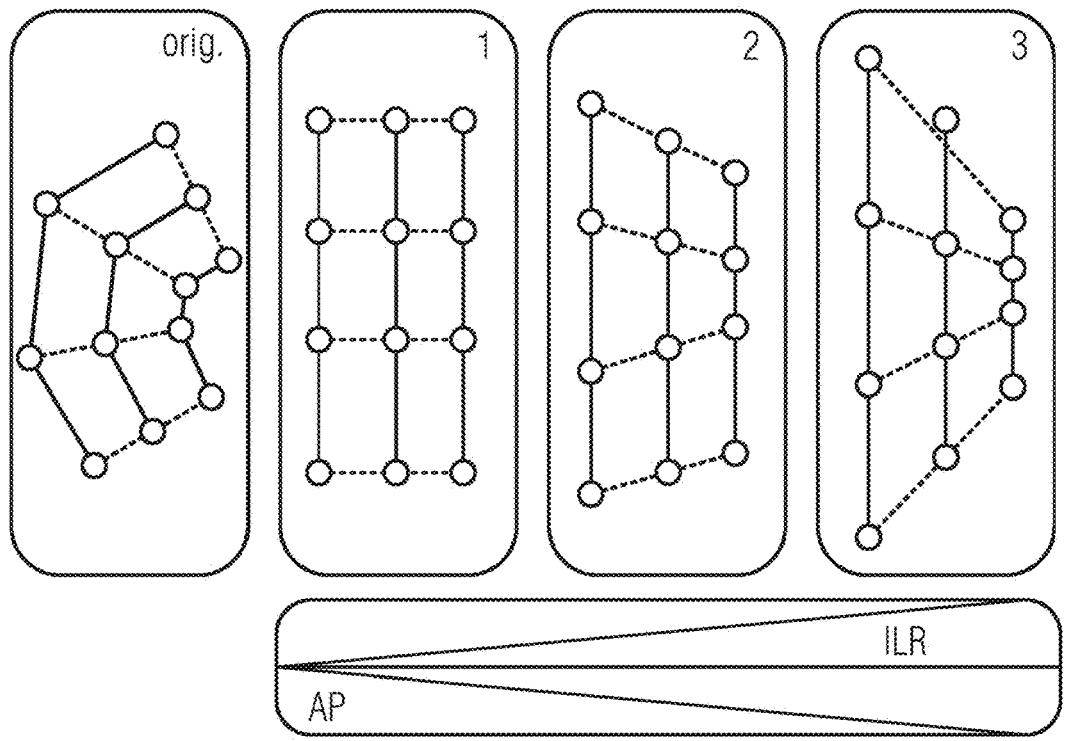
FIG. 6 shows, by way of example, the phenomenon of angular distortion and length distortion with reformatting of a volume.

Since the ADR surface (the three-dimensional parameterized surface) is not planar as a rule, the surface size of the triangles of the offset surfaces differs from the corresponding triangles of the ADR surface, as can be seen in FIG. 6 in the left-hand component drawing identified by orig. The extent of the reduction or enlargement depends on the curvature of the ADR surface 2 at the corresponding location and is different over the entire grid. The use of the same geometry for all ADR surfaces, as is the case in the example embodiment in FIG. 5 and in the component drawing designated number 1 in FIG. 6, therefore involves a volume distortion, so no rigidity ILR prevails locally. To take account of the different sizes of the triangles in the different offset surfaces, the two-dimensional grids of the different slices are modified in the reformatted representation in such a way that they now have differently dimensioned triangles with different nodes. In other words, a shared three-dimensional grid is then extended to all slices and the local and global reformatting then carried out for all slices. The associated two-dimensional grid results as follows:

$$v' \leftarrow [v'_0 \ldots v'_{n-1}, v'_n \ldots v'_{2n-1}, v'_{2n} \ldots v'_{3n-1}] \quad (9)$$

The indices 0 to n1 are associated, for example, with the lower slice of a stack of slices, the indices n to 2n1 with the middle slice and 2n to 3n1 with the upper slice of a slice stack. The v' are nodes analogous to those of the grid in equation 1.

The topological information relating to the reformatted triangles T' and the reformatted half-edges HE' is expanded accordingly. This is accompanied by a trifold expansion in the number of unknowns in equation system 7. The individual triangles of the offset surfaces are therefore imaged with the greatest possible rigidity ILR in the two-dimensional representation. This is illustrated in the component drawing of FIG. 6 designed by the number 3. However, the rigidity comes at the expense of a lower conformality AP, so what are known as shear effects occur.

To achieve a compromise between these two extremes, an additional shear term can be added to the energy functional of equation 6. One aim here is to keep the nodes $V_i$ of the offset slices and the middle slice at similar relative positions in respect of the local tangent space. For this, first of all an offset $o_i^-$ or $o+_i$ is determined for each offset surface for each node individually. To calculate this offset, first of all the nodes $v_i^-$ or $v_i^+$ are transformed into the tangent space of the ADR surface with the associated node $V_i$. Since the transformations $N_t$ are defined only for triangles and generally a plurality of triangles rest on one node, the offsets contributed by various triangles $t \in T(i)$ are averaged to obtain an averaged offset $o_i^-$ or $o+_i$ of each node. The averaged offsets are calculated as follows therefore:

$$o_i^- = \frac{1}{\#T(i)} \sum_{t \in T(i)} R_t(N_t(v_i^-)) \quad (10)$$
$$o_i^+ = \frac{1}{\#T(i)} \sum_{t \in T(i)} R_t(N_t(v_i^+))$$
$$\forall i = 0 \ldots n-1$$

where $T(i)$ is a set of triangles which rest on the node $V_i$ of the middle slice. $\#T(i)$ comprises the number of triangles of the set of triangles. The two offsets $o_i^-$ and $o+_i$ depend only on the geometry of the initial ADR surface and are constant during the optimization of the ADR surface or corresponding surface stack.

The different offsets are then also considered in the energy term of equation 6, with the shear term already mentioned being added. The volume energy resulting from this is calculated as follows:

$$E_{VOL}^\alpha(v'_i, R) = E(v'_i, R) + \alpha E_{shear}(v'_i, R) \quad (11)$$

the shear term $E_{shear}$ is composed as follows here:

$$E_{shear}(v'_i, R) = \sum_{i=0 \ldots n-1} \|(v'_{i+n} - v'_i) - o_i^-\|^2 + \|(v'_{i+n} - v'_{i+2n}) - o_i^+\|^2 \quad (12)$$

The weighting a allows the effect of the shear term to change. Equation 11, in conjunction with equation 12, limits the nodes of the offset slices to offsets which are similar to those of the nondeformed state. An excessive angular distortion, i.e. shearing, of the offset slices relative to each other is therefore avoided. A larger a leads to a formatted volume having a lower angular distortion but a length distortion that is all the greater, and vice versa. A compromise between angular distortion and rigidity is therefore achieved with a mean value for a, and this is illustrated by the component drawing of FIG. 6 identified by 2. The positive and negative slices are both shifted by a particular, previously defined distance d from the middle slice.

During the step of sampling, consideration must be given to the fact that calculation of the barycentric coordinates is now dependent on the z position, i.e. the position in the offset direction of the respective triangles. An interpolation has to be carried out in this case therefore. More precisely, a type of linear mixing is applied. A triangle with a particular height z is therefore defined as follows:

$$T(z) = u * (v'_{a-n}, v'_{b-n}, v'_{c-n}) + v * (v'_a, v'_b, v'_c) + w * (v'_{a+n}, v'_{b+n}, v'_{c+n}), \quad (13)$$

$$z \in [0, 2d]$$

$$\text{where } u = \begin{cases} \left(1 - \dfrac{z}{d}\right) & 0 < z < d \\ 0 & d < z < 2d \end{cases}$$

$$v = \begin{cases} \dfrac{z}{d} & 0 < z < d \\ 1 - \dfrac{z-d}{d} & d < z < 2d \end{cases}$$

$$w = \begin{cases} 0 & 0 < z < d \\ \dfrac{z-d}{d} & d < z < 2d \end{cases}$$

Here $(v'_{an}, v'_{bn}, v'_{cn})$, $(v'_a, v'_b, v'_c)$, $(v'_{a+n}, v'_{b+n}, v'_{c+n})$ are the instances of a triangle in the negative or bottom, middle, and the positive or top ADR slice. Since triangles then comprise different pixels as a function of z, a type of mixing of the regions enclosed by the half-edges of a triangle is then performed in all slices if they were listed in a lookup table for sampling.

As described in the preceding paragraphs, distortions in two-dimensional imaging can be reduced but basically not prevented. Since some regions of the ADR image surface are more important that others, however, it can be advantageous to consider these as early as during reformatting. For this purpose, it is expedient to use importance maps with which the distribution of the distortions can be controlled during reformatting. The errors or distortions in particular regions having greater importance can therefore be reduced, for which a greater degree of distortions is accepted in the regions with lower priority in return.

To be able to control the distortions during reformatting, a weight $w_i$ is allocated to each of the nodes $v_i$ according to the importance of a region. This allocation can occur, for example, in advance by particular weights being allocated to particular regions in an ADR reference grid. Alternatively, the weights can also be allocated interactively in a reformatted representation, with the reformatting process then being started again. For example, in the case of representation of skeletal parts, masks can be generated for the skeletal regions by defining threshold values and reworking the initial image. These masks can be used directly to allocate the weights to the nodes of an ADR surface, so the distortions are reduced in the regions having the skeletal parts.

In order to also consider the weights in the reformatting they have to also be incorporated in the calculation of the energy according to equation 6 or in equation system 7. Here each term in equation 6 is multiplied by the weight of the respective half-edge $w_{(i,j)}$, with these weights representing the average $w_{(i,j)}=0.5*(w_i+w_j)$ of the weights $w_i$ and $w_j$ of the nodes pertaining to the respective half-edge. The equation system while taking the shear energy $E_{shear}$ and weights $w_{(i,j)}$ into consideration then results as follows:

$$\sum_{j \in V(i)} w_{(i,j)}(\cot(\Theta_{i,j}) + \cot(\Theta_{j,i}))(v'_i - v'_j) + A_i = \quad (14)$$

$$\sum_{j \in V(i)} w_{(i,j)}(\cot(\Theta_{i,j})R_{t(i,j)} + \cot(\Theta_{j,i})R_{t(j,i)})(v^0_i - v^0_j) + B_i$$

$$\forall\, i = 0 \ldots 3n-1$$

$A_i$ and $B_i$ result from the shear term and connect the individual ADR slices:

$$A_i = \begin{cases} v'_i - v'_{n+i} & i < n \\ 2v'_i - v'_{i-n} - v'_{i+n} & n < i < 2n \\ v'_i - v'_{i-n} & 2n < i < 3n \end{cases} \quad (15)$$

$$B_i = \begin{cases} -o^-_i & i < n \\ -o^-_{i-n} + o^+_{i-n} & n < i < 2n \\ -o^+_{i-2n} & 2n < i < 3n \end{cases} \quad (16)$$

The left-hand side of equation 14 has constant coefficients and the corresponding linear system is thinly populated and symmetrical. The coefficients can therefore be defined once and then be retained during the iterations. By contrast, the rotations $R_t$ on the right-hand side must be re-calculated with each iteration since they depend on the geometry of the current solution.

The described example embodiment, which illustrates an imaging method having three slices in detail, can be expanded to any number of slices. With a greater number of imaged slices the distortions are minimized even more finely by the optimized grid. The number of offset surfaces can therefore be chosen randomly. The connections or edges and the energy term according to equation 12 can be generalized to any number of slices without additional difficulties.

In contrast to the approaches according to the prior art, the inventive method can be used for a large range of different anatomical structures. The example embodiments described in detail are limited to skeletal parts but the method can also be applied to completely different anatomical structures.

Figure 7:
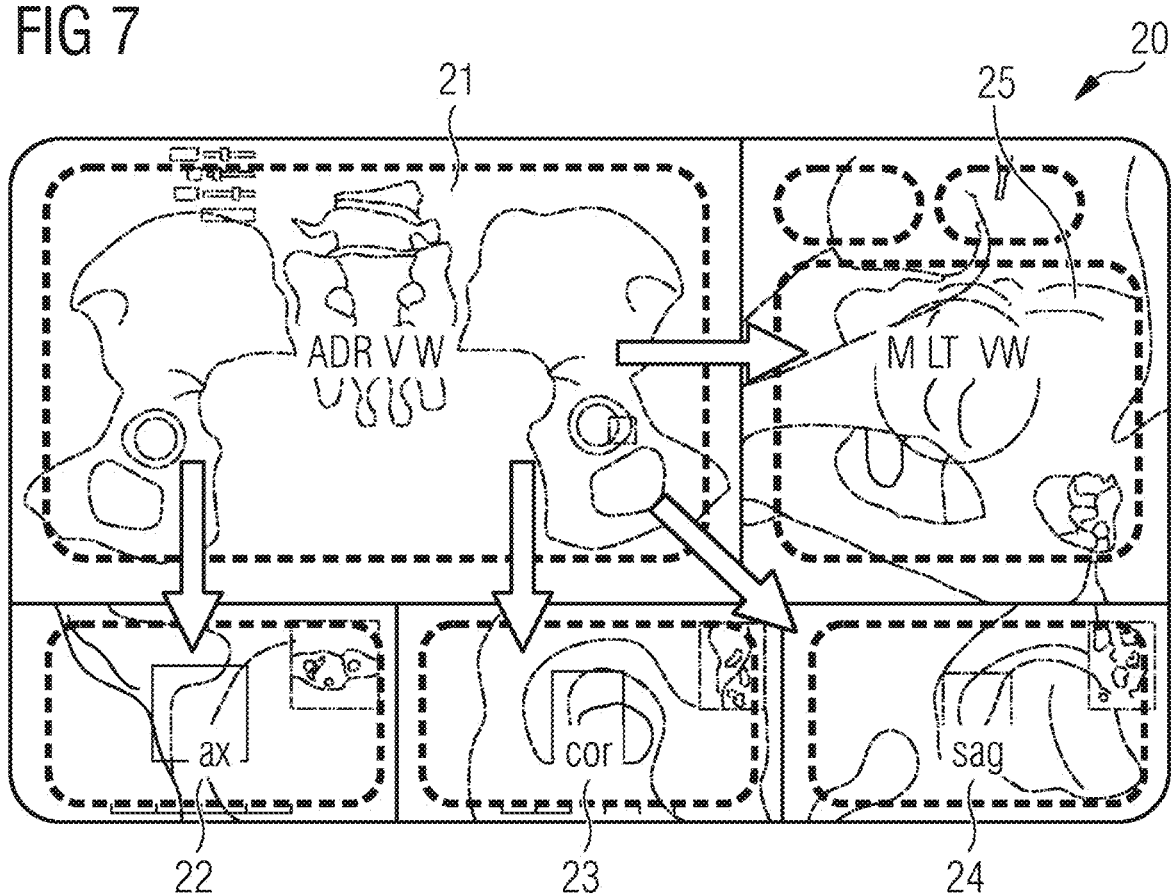
FIG. 7 shows a user interface which comprises a reformatted two-dimensional image of a three-dimensional object to be examined as a navigation surface, and also various views of the three-dimensional object.

To be able to effectively use the generated ADR images it is expedient to classify these images in a suitable medical visualization environment. FIG. 7 shows a suitable user interface 20 for this visualization environment. The visualization environment is divided in such a way that the ADR image 21, also designated ADRVW (ADR view), is positioned top left while cross-sections of the image recording can be seen in the lower region. Cross-section 22 is a representation in the axial direction which is also identified by ax in FIG. 7. Cross-section 23 is a representation in the coronal direction, which is designated by cor in FIG. 7, and cross-section 24 is a representation in the sagittal direction which is designated by sag in FIG. 7. A perspective view 25, also called MLTVW (multi view), can be seen top right. In this visualization environment the ADR image 21 is used for navigation in the other images because the overview for the user is most likely given in the ADR image. The different views are linked with each other in such a way that the other views also change as a function of the position in the view in the ADR image 21. If, for example, the position of the square, which defines a position of the detailed views 22 to 24, arranged in the ADR image to the right below the center of the image is shifted, the views 22 to 24 also change accordingly. The squares arranged centrally in the views 22 to 24 correspond to the image detail defined by the square in the ADR image.

Figure 8:
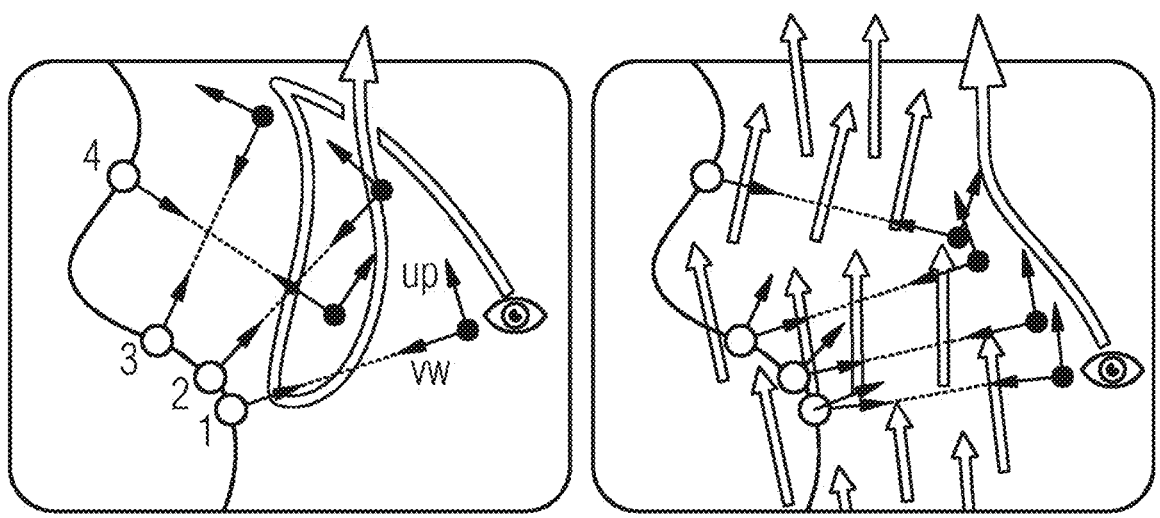
FIG. 8 shows the defining of a position and the viewing angle of a camera using normals on a vector field derived from the parameterized three-dimensional surface.

If the viewer changes the position in the ADR image, the viewing angle for the perspective view 25 changes, in other words the camera perspective is more or less changed, with the position of the virtual camera, the viewing direction and the camera rotation playing a part in a dynamic process. FIG. 8 illustrates a scenario of this kind. To calculate the viewing direction vw in the perspective view, the corresponding normal can be used on the three-dimensional surface grid. The positive normal vector can be defined as the direction of the camera position and the negative normal vector as the viewing direction vw. Due to the curvature of the ADR surfaces, orientation of the camera position using the normals of the ADR surfaces leads to unsteady camera movement, as is illustrated in the left-hand component drawing in FIG. 8. In addition to the viewing direction vw, FIG. 8 also shows the upwards direction up of the viewer or camera oriented perpendicular thereto. To achieve a continuous camera movement, a vector field is defined along the three-dimensional surface grid using vertex skinning techniques and also adjusted accordingly during the optimization processes of the two-dimensional grid. The normals on the vectors generated with the vertex skinning techniques produce the steadied camera position.

Figure 9:
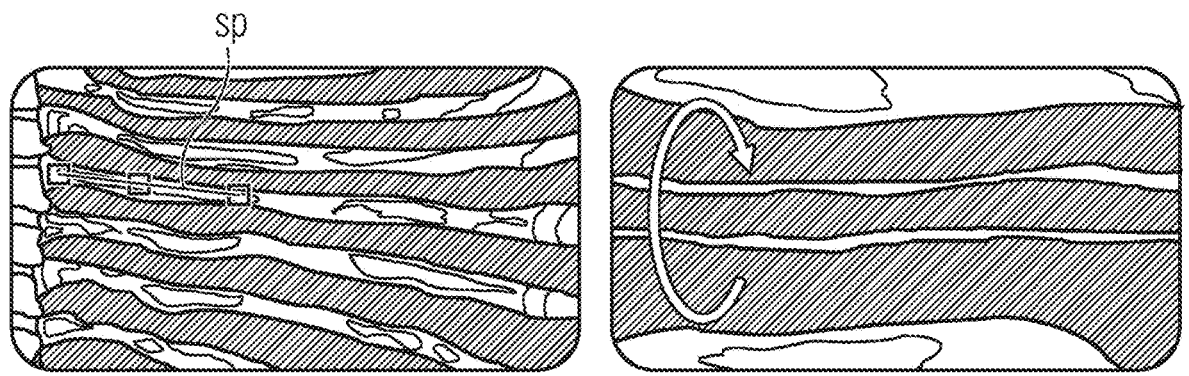
FIG. 9 shows a CPR visualization on the basis of a reformatted two-dimensional representation.

The combination of the ADR images with a PR visualization, as is shown in FIG. 9, can constitute an additional possibility for obtaining an improved view. Here a spline sp is firstly defined in the ADR image, and this defines the characteristic of a center of rotations around which a CPR visualization of a section of the recorded object should be carried out. The spline defined in the ADR image is then converted into the three-dimensional image space of the recording and can be used to implement a CPR visualization around the defined center.

Figure 10:
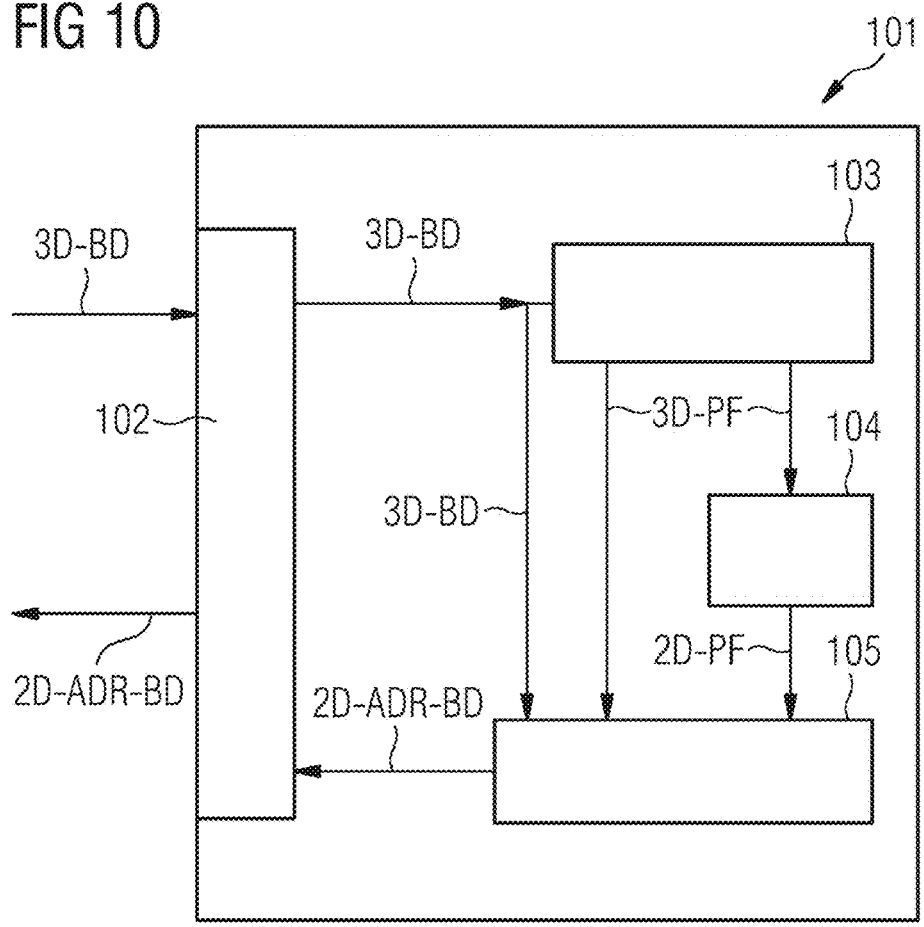
FIG. 10 shows a device for two-dimensional imaging of a three-dimensional object to be examined.

FIG. 10 shows a device 101 for two-dimensional imaging of a three-dimensional object to be examined. An interface unit 102 comprises an input interface and an output interface, which acquires the image data of a recorded 3D image 3DBD of a three-dimensional object to be examined and outputs the created two-dimensional ADR image data 2DADRBD. The acquired 3D image date 3DBD is transferred to a surface grid-determining unit 103. This has the function of defining a three-dimensional parameterized surface which is conformal with the anatomical structure of the three-dimensional object to be examined. The data of the three-dimensional parameterized surface 3DPF is transferred to a reformatting unit 104 which images the three-dimensional parameterized surface onto a two-dimensional parameterized surface. The data of the parameterized two-dimensional surface 2DPF and the remaining image data 3DBD and 3DPF is transferred to a sampling unit 105. This has the function of imaging the three-dimensional object to be examined by imaging image points associated with the three-dimensional parameterized surface onto the two-dimensional parameterized surface. The ADR image data generated in the process is transferred by way of the interface unit 102 to, for example, an output unit or a storage unit (not shown).

The described methods allow the user to evaluate the image material generated with the medical imaging methods quickly and effectively. The methods described in detail can be used flexibly with very different examination objects, and this reduces the effort for the user and increases the efficiency of use of this method.

In conclusion reference is again made to the fact that the methods and structures described in detail above are only example embodiments and that the basic principle can also be varied within wide ranges by a person skilled in the art without departing from the field of the invention insofar as it is specified by the claims. For the sake of completeness, reference is also made to the fact that the use of the indefinite article "a" or "an" does not preclude the relevant features from also being present multiple times. Similarly, the term "unit" or "module" does not preclude this from comprising a plurality of components which can optionally also be spatially distributed.

The invention claimed is:

1. A method of imaging a three-dimensional object to be examined, the method comprising:
    creating, via a processor, a conformal three-dimensional parameterized surface, based on an anatomical structure of the three-dimensional object to be examined;
    imaging, via the processor, image points associated with the created conformal three-dimensional parameterized surface onto a two-dimensional parameterized surface; and
    mapping via the processor, a two-dimensional representation that conforms to the conformal three-dimensional parameterized surface of the three-dimensional object to be examined.

2. The method of claim 1, wherein the conformal three-dimensional parameterized surface is parameterized by a three-dimensional surface grid including a number of individual elements,
    the two-dimensional parameterized surface is parameterized by a two-dimensional grid including a number of individual elements, and
    the conformal two-dimensional representation of the three-dimensional object to be examined is created by imaging image points associated with the individual elements of the three-dimensional surface grid onto the individual elements of the two-dimensional grid.

3. The method of claim 2, wherein the individual elements include at least one of triangles, rectangles, hexagons and other polygons and wherein the three-dimensional surface grid is a regular grid or an irregular grid.

4. The method of claim 2, wherein the conformal three-dimensional parameterized surface is an open surface or a closed surface, converted before imaging of the three-dimensional parameterized surface onto a two-dimensional parameterized surface into an open three-dimensional parameterized surface.

5. The method of claim 4, wherein the individual elements include at least one of triangles, rectangles, hexagons and other polygons and wherein the three-dimensional surface grid is a regular grid or an irregular grid.

6. The method of claim 2, wherein the imaging is achieved by optimizing an energy term associated with the three-dimensional parameterized surface and a two-dimensional parameterized surface to be optimized.

7. The method of claim 2, wherein, in addition to the conformal three-dimensional parameterized surface, a plurality of three-dimensional parameterized offset surfaces, conformal with the anatomical structure of the three-dimensional object to be examined, are generated and wherein each are imaged onto a two-dimensional parameterized surface, so the three-dimensional object is imaged onto a three-dimensional slice stack comprising two-dimensional surfaces.

8. The method of claim 2, wherein the method further comprises one of the following:
    a) annotation of at least one of points, regions and structures in the image,
    b) at least one of interactive refinement and shifting of the image based on current image, and
    c) generation of detailed views.

9. The method of claim 1, wherein the conformal three-dimensional parameterized surface is an open surface or a closed surface, converted before imaging of the conformal three-dimensional parameterized surface onto the two-dimensional parameterized surface into an open three-dimensional parameterized surface.

10. The method of claim 1, wherein the imaging is achieved by optimizing an energy term associated with the conformal three-dimensional parameterized surface and the two-dimensional parameterized surface to be optimized.

11. The method of claim 10, wherein a rigidity within slices and an angular distortion between slices is modeled separately with the energy term.

12. The method of claim 10, wherein when the imaging of the three-dimensional parameterized surfaces onto one or more two-dimensional parameterized surface takes place, at least one of a local distortion of the image is chosen as a function of an importance of image regions of the three-dimensional object and of different importance of the image regions is taken into consideration by way of weighting factors in the energy term to be optimized.

13. The method of claim 1, wherein, in addition to the conformal three-dimensional parameterized surface, a plurality of three-dimensional parameterized offset surfaces, conformal with the anatomical structure of the three-dimensional object to be examined, are generated and wherein each are imaged onto a two-dimensional parameterized surface, so the three-dimensional object is imaged onto a three-dimensional slice stack comprising two-dimensional surfaces.

14. The method of claim 13, wherein the three-dimensional parameterized offset surfaces are defined by determining normal vectors orthogonal to the three-dimensional parameterized surface.

15. The method of claim 13, wherein the three-dimensional parameterized offset surfaces comprise offset surface grids smoothed by applying grid smoothing methods, wherein overlappings of adjacent normal vectors are avoided.

16. The method of claim 15, wherein the three-dimensional offset surface grids are explicitly calculated.

17. The method of claim 13, wherein when the imaging of the three-dimensional parameterized surfaces onto one or more two-dimensional parameterized surface takes place, at least one of a local distortion of the image is chosen as a function of the importance of image regions of the three-dimensional object and the different importance of the image regions is taken into consideration by way of weighting factors in the energy term to be optimized.

18. The method of claim 1, wherein the method further comprises one of the following:

a) annotation of at least one of points, regions and structures in the image,
b) at least one of interactive refinement and shifting of the image based on a current image, and
c) generation of detailed views.

19. A method for representing a section of an object to be examined, the method comprising:
carrying out the method of claim 1;
defining a section for representation of the object to be examined by identification in the two-dimensional representation; and
carrying out a visualization method in the section for representation.

20. A device for imaging a three-dimensional object to be examined, comprising:
memory storing computer-readable instructions; and
one or more processors configured to execute the computer-readable instructions such that the one or more processors are configured to perform operations including,
creating a conformal three-dimensional parameterized surface based on an anatomical structure of the three-dimensional object to be examined;
imaging the conformal three-dimensional parameterized surface onto a two-dimensional parameterized surface; and
mapping a two-dimensional representation that conforms to the conformal three-dimensional parameterized surface.

* * * * *